US006255561B1

(12) United States Patent
Kossman et al.

(10) Patent No.: US 6,255,561 B1
(45) Date of Patent: Jul. 3, 2001

(54) NUCLEIC ACID MOLECULES CODING FOR DEBRANCHING ENZYMES FROM MAIZE

(75) Inventors: Jens Kossman, Golm; Lothar Willmitzer, Berlin; Michael Emmermann, Bergholz Rehbrücke, all of (DE)

(73) Assignee: PlantTec Biotechnologie GmbH, Potsdam (DE)

( * ) Notice: Subject to any disclaimer, the term of this patent is extended or adjusted under 35 U.S.C. 154(b) by 0 days.

(21) Appl. No.: 09/148,680

(22) Filed: Sep. 4, 1998

Related U.S. Application Data

(63) Continuation of application No. PCT/EP97/01141, filed on Mar. 6, 1997.

(30) Foreign Application Priority Data

Mar. 7, 1996 (DE) ............................................. 196 08 918

(51) Int. Cl.$^7$ .............................. C12N 15/29; C12N 5/04; C12N 15/82; C12P 19/04; A01H 5/00
(52) U.S. Cl. ....................... 800/284; 800/317.2; 800/320; 800/320.1; 435/69.1; 435/101; 435/252.3; 435/320.1; 435/412; 435/417; 435/419; 536/23.6
(58) Field of Search ........................... 536/23.6; 435/69.1, 435/320.1, 101, 412, 419, 417, 252.3; 800/284, 317.2, 320, 320.1

(56) References Cited

U.S. PATENT DOCUMENTS

| | | | |
|---|---|---|---|
| 4,454,161 | 6/1984 | Okada et al. | 426/48 |
| 6,001,628 | 12/1999 | Kossmann et al. | 435/210 |
| 6,057,493 | 5/2000 | Willmitzer et al. | 800/284 |
| 6,066,782 | 5/2000 | Kossmann et al. | 800/284 |
| 6,117,665 | 9/2000 | Kossmann et al. | 435/210 |

FOREIGN PATENT DOCUMENTS

| | | | |
|---|---|---|---|
| 19028/95 | 10/1995 | (AU) . | |
| 0 479 359 A1 | 4/1992 | (EP) . | |
| 0 529 894 A1 | 3/1993 | (EP) | A23L/1/09 |
| 0 554 122 A1 | 8/1993 | (EP) | A01H/1/02 |
| WO 92/11376 | 7/1992 | (WO) . | |
| WO 92/11382 | 7/1992 | (WO) | C12P/21/00 |
| WO 92/14827 | 9/1992 | (WO) . | |
| WO 95/04826 | 2/1995 | (WO) | C12N/15/56 |
| WO 95/09922 | 4/1995 | (WO) | C12N/15/62 |
| WO 96/03513 | 2/1996 | (WO) | C12N/15/55 |
| WO 96/19581 | 6/1996 | (WO) | C12N/15/56 |

OTHER PUBLICATIONS

Kossman et al. Progress Biotechnol. 10—271–278, 1995.*
Hawker, J.S. et al., "Interaction of Spinach Leaf Adenosine Diphosphate Glucose α–1,4–Glucan α–4–Glucosyl Transferase and α–1,4–Glucan, α–1,4–Glucan–6–Glycosyl Transferase in Synthesis of Branhced α–Glucan", *Archives of Biochemistry and Biophysics*, 160, 530–551 (1974).

Hobson, P.N. et al., "The Enzymic Synthesis and Degradation of Starch—Part XIV—R–Enzyme", *Journal of the Chemical Society*, 1451–1459 (1951).

Ishizaki, Y. et al., "Debranching Enzymes of Potato Tubers (*Solanum tuberosum* L.). I. Purification and Some Properties of Potato Isoamylase", *Agric. Biol. Chem.*, 771–779 (1983).

Katsuragi, N. et al., "Entire Nucleotide Sequence of the Pullulanese Gene of *Klebsiella aerogenes* W70", *Journal of Bacteriology*, 169, 2301–2306 (1987).

Li, B. et al., "Characterization and Subcellular Localization of Debranching Enzyme and Endoamylase from Leaves of Sugar Beet", *Plant Physiology*, 98, 1277–1284 (1992).

Ludwig, I. et al., "Purification and Properties of Spinach Leaf Debranching Enzyme", *Plant Physiology*, 74, 856–861 (1984).

Schaller, A., "The Electronic Plant Gene Register", *Plant Physiology*, 108, 1341–1343 (1995).

Shannon, J.C. et al., "Genetics and Physiology of Starch Development", *Starch: Chemistry and Technology*, 2d Ed., Academic Press, 25–86 (1984).

Visser, R.G.F. et al., "Inhibition of the expression of the gene for granule–bound starch synthase in potato by antisense constructs", *Mol. Gen. Genet.*, 225, 289–296 (1991).

R.C. Black et al, (1996) "Genetic Interactions Affecting Maize Phytoglycogen and the Phytoglycogen–Forming Branching Enzymes", *Genetics*, 53, pp. 661–668.

D.C. Doehlert et al., (1991) "Two Classes of Starch Debranching Enzymes From Developing Maize Kernels", *J. Plant Physiol.*, 138, pp. 566–572.

L. C. Hannah et al., (1993) "Biotechnological Modification of Carbohydrates for Sweet Corn and Maize Improvement", *Scientia Horticulturae*, 55, pp. 177–197.

M.G. James et al., (1995) "Characterization of the Maize Gene *Sugary 1*, a Determinant of Starch Composition in Kernels", *The Plant Cell*, 7, pp. 417–429.

D.J. Manners et al., (1969) "Studies on Carbohydrates–Metabolising Enzymes: Part XX Sweet–Corn Debranching Enzymes", *Carbohyd. Res.*, 9, pp. 107–121.

D. Pan et al., (1984) "A Debranching Enzyme Deficiency in Endosperms of the *Sugary–1* Mutants of Maize, " *Plant Physiol.*, 74, pp. 324–328.

* cited by examiner

*Primary Examiner*—David T. Fox
(74) *Attorney, Agent, or Firm*—Fish & Neave; James F. Haley, Jr.; Li Su

(57) ABSTRACT

Nucleic acid molecules are described, which encode debranching enzymes from maize, as well as transgenic plant cells and plants in which an amylopectin with modified properties is synthesized due to the expression of a debranching enzyme from maize or due to the inhibition of such an endogeneous debranching enzyme activity.

26 Claims, No Drawings

NUCLEIC ACID MOLECULES CODING FOR DEBRANCHING ENZYMES FROM MAIZE

CROSS-REFERENCE TO RELATED APPLICATION

This application is a continuation of international application PCT/EP97/01141, filed Mar. 6, 1997, which designated the United States.

FIELD OF THE INVENTION

The present invention relates to nucleic acid molecules encoding proteins from maize with the enzymatic activity of a debranching enzyme (R enzyme). The invention further relates to transgenic plants and plant cells, in which an amylopectin with an altered degree of branching is synthesized due to the expression of an additional debranching enzyme activity from maize or due to the inhibition of an endogeneous debranching enzyme activity. The invention also relates to the starch obtainable from said transgenic plant cells and plants.

Starch plays an important role as storage substance in a multitude of plants and also as a regenerative, industrially usable raw material and has gained increasing significance. For the industrial use of starch it is necessary that it meets the demands of the processing industry with respect to its structure, form and/or other physico-chemical parameters. In order to enable the use in as many areas as possible it is furthermore necessary to achieve a large variety of substances.

The polysaccharide starch is made up of chemically homogeneous basic components, namely the glucose molecules. However, it constitutes a highly complex mixture of various types of molecules which differ from each other in their degree of polymerization and in the degree of branching. One differentiates between amylose-starch, a basically non-branched polymer made up of α-1,4-glycosidically branched glucose molecules, and amylopectin-starch, a branched polymer, in which the branching results from additional α-1,6-glycosidic interlinkings.

In plants used typically for the production of starch, such as maize or potato, the synthesized starch consists of approximately 25% amylose-starch and of about 75% amylopectin-starch. In the case of maize, for example, a further branched polysaccharide, apart from amylopectin, occurs, namely the so-called phytoglycogen which differs from amylopectin by exhibiting a higher degree of branching and different solubility (see e.g. Lee et al., Arch. Biochem. Biophys. 143 (1971), 365–374; Pan and Nelson, Plant Physiol. 74 (1984), 324–328). In the scope of the present application the term amylopectin is used in such a way as to comprise the phytoglycogen.

With respect to the homogeneity of the basic component starch for its use in the industrial area, starch-producing plants are needed which contain, for example, only the component amylopectin or only the component amylose. For a number of other uses plants are needed that synthesize amylopectin types with different degrees of branchings.

Such plants may for example be obtained by breeding or by means of mutagenesis techniques. It is known for various plant species, such as for maize, that by means of mutagenesis varieties may be produced in which only amylopectin is formed. Also in the case of potato a genotype was produced from a haploid line by means of chemical mutagenesis. Said genotype does not form amylose (Hovenkamp-Hermelink, Theor. Appl. Genet. 75 (1987), 217–221).

From Visser et al. (Mol. Gen. Genet. 225 (1991), 289) and WO 92/11376 it is furthermore known that by means of an antisense-inhibition of the gene of the granule-bound starch synthase in potato varieties may be produced that mainly synthesize pure amylopectin. Moreover, DNA sequences are known from WO 92/14827 that encode a branching enzyme (Q enzyme), that introduces α-1,6 branchings into amylopectin starch. By means of these DNA sequences it should be possible to produce transgenic plants in which the amyloselamylopectin ratio of the starch is altered.

For a further targeted modification of the degree of branching of starch synthesized in plants by means of recombinant DNA techniques, it is still necessary to identify DNA sequences that encode enzymes participating in the starch metabolism, particularly in the branching of starch molecules.

Apart from the Q enzymes that introduce branchings into starch molecules, enzymes occur in plants which are capable of dissolving branchings. These enzymes are called debranching enzymes and are classified as three groups according to their substrate specifity:

(a) Pullulanases which also, apart from pullulan, use amylopectin as a substrate, occur in microorganisms, e.g. Klebsiella, and in plants. In plants these enzymes are also called R enzymes.

(b) Isoamylases, which do not use pullulan, but glycogen and amylopectin as a substrate, also occur in microorganisms and plants. Isoamylases were described for example in the case of maize (Manners & Rowe, Carbohydr. Res. 9 (1969), 107) and potato (Ishizaki et al., Agric. Biol. Chem. 47 (1983), 771–779).

(c) Amylo-1,6-glucosidases were described in the case of mammals and yeast; as a substrate, they make use of dextrines.

In the case of sugar beet, Li et al. (Plant Physiol. 98 (1992), 1277–1284) could only prove the occurrence of one debranching enzyme of the pullulanase type, apart from five endo- and two exoamylases. This enzyme having a size of approximately 100 kD and an optimum pH value of 5.5 is located within the chloroplasts. A debranching enzyme using pullulan as a substrate was also described for spinach. The debranching enzyme from spinach as well as that from sugar beet exhibit a fivefold lower activity in a reaction with amylopectin as substrate when compared to a reaction with pullulan as a substrate (Ludwig et al., Plant Physiol. 74 (1984), 856–861; Li et al., Plant Physiol. 98 (1992), 1277–1284).

In the case of the agriculturally significant starch-storing cultured plant potato, the activity of a debranching enzyme was examined by Hobson et al. (J. Chem. Soc., (1951), 1451). It was proven that the respective enzyme, contrary to the Q enzyme, does not exhibit any activities leading to an elongation of the polysaccharide chain, but merely hydrolyses α-1,6-glycosidic bonds. So far, however, the enzyme could not be characterized in more detail.

In the case of potato, methods for the purification of the debranching enzyme as well as partial peptide sequences of the purified protein have already been proposed (WO 95/04826).

The purification of a debranching enzyme and the isolation of a corresponding cDNA has by now been described for spinach (Renz et al., Plant Physiol. 108 (1995), 1342).

For the most significant starch-delivering plant, namely maize, so far only the existence of one debranching enzyme was described in the prior art. Due to its substrate specificity, this debranching enzyme is classified as an isoamylase (see e.g. Hannah et al., Scientia Horticulturae 55 (1993), 177–197 or Garwood (1984) in Starch Chemistry and Technology, Whistler, R. L., BeMiller, J. N., Puschall, E. F. (eds.), Academic Press San Diego, New York, Boston, 25–86). The corresponding mutant was designated su (sugary). The gene of the sugary locus was cloned recently (see James et al., Plant Cell 7 (1995), 417429). So far no other gene locus apart from the sugary locus is known for maize, which encodes a protein with debranching enzyme activity. Thus, there is so far no indication as to the existence of further types of debranching enzymes from maize. If transgenic maize plants are to be produced which no longer exhibit any debranching enzyme activity, e.g. in order to achieve a modification of the degree of branching of the arryiopectin starch, it is necessary to identify all debranching enzymes occurring in maize and to isolate the corresponding genes or cDNA sequences.

Therefore, the technical problem underlying the present invention is to identify further debranching enzymes possibly occurring in maize and to isolate corresponding nucleic acid molecules encoding these enzymes.

This problem is solved by the provision of the embodiments as defined in the claims.

SUMMARY OF THE INVENTION

Thus, the present invention relates to nucleic acid molecules encoding proteins with the biological activity of a debranching enzyme from maize or a biologically active fragment thereof, wherein such nucleic acid molecules preferably encode a debranching enzyme from maize that exhibits the amino acid sequence depicted in SEQ ID No. 2. In a particularly preferred embodiment such a nucleic acid molecule comprises the nucleotide sequence depicted under SEQ ID No. 1, in particular the coding region, or a corresponding ribonucleotide sequence.

The present invention also relates to nucleic acid molecules encoding proteins with the biological activity of a debranching enzyme from maize or biologically active fragments thereof and hybridizing to one of the above-described nucleic acid molecules.

Furthermore, the present invention relates to nucleic acid molecules the sequences of which differ from the sequences of the above-described nucleic acid molecules due to the degeneracy of the genetic code and which encode a protein exhibiting the biological activity of a debranching enzyme from maize.

The invention also relates to nucleic acid molecules the sequence of which is complementary to the complete or partial sequence of the above-described nucleic acid molecule.

DETAILED DESCRIPTION OF THE INVENTION

In the scope of the present invention the term "hybridization" signifies hybridization under conventional hybridizing conditions, preferably under stringent conditions, as described for example in Sambrook et al., Molecular Cloning, A Laboratory Manual, 2nd Edition (1989) Cold Spring Harbor Laboratory Press, Cold Spring Harbor, N.Y.). Nucleic acid molecules hybridizing to the nucleic acid molecules of the invention may basically be derived from any desired type of maize plant.

Nucleic acid molecules hybridizing to the molecules of the invention may for example be isolated from genomic or cDNA libraries.

The identification and isolation of such nucleic acid molecules from maize plants may take place by using the molecules of the invention or parts of these molecules or, as the case may be, the reverse complements of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequence indicated under Seq ID No. 1 or parts thereof. The fragments used as hybridization probe may also be synthetic fragments which were produced by means of the conventional synthesizing methods and the sequence of which is basically identical to that of a nucleic acid molecule of the invention. After identifying and isolating the genes hybridizing to the nucleic acid sequences of the invention, the sequence has to be determined and the properties of the proteins encoded by this sequence have to be analyzed.

The molecules hybridizing to the nucleic acid molecules of the invention also comprise fragments, derivatives and allelic variants of the above-described DNA molecules which encode a debranching enzyme from maize or a biologically, i.e. enzymatically active fragment thereof. In this context, fragments are defined as parts of the nucleic acid molecules, which are long enough in order to encode a polypeptide with the enzymatic activity of a debranching enzyme from maize. In this context, the term derivative means that the sequences of these molecules differ from the sequences of the above-mentioned nucleic acid molecules at one or more positions and that they exhibit a high degree of homology to these sequences. In this regard, homology means a sequence identity of at least 40%, in particular an identity of at least 60%, preferably of more than 80% and still more preferably a sequence identity of more than 90%. The deviations occurring when compared to the above-described nucleic acid molecules might have been caused by deletion, addition, substitution, insertion or recombination.

Moreover, homology means that the respective nucleic acid molecules or the proteins they encode are functionally and/or structurally equivalent. The nucleic acid molecules which are homologous to the above-described molecules and represent derivatives of these molecules, are generally variations of these molecules, that constitute modifications exerting the same biological function. These variations may be naturally occurring variations, for example sequences derived from other organisms, or mutations, wherein these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability; pH-optimum, temperature-optimum etc.

The enzymatic activity of the debranching enzyme may for example be shown by means of a staining test, as described in WO 95/04826. This test is based on the fact that a protein with a starch-modifying activity may be shown by separating protein extracts, for example from maize kernel, on non-denaturing amylopectin-containing polyacrylamide gels (PAAG) and the gel is subsequently, after incubation with a suitable buffer, subjected to iodine staining. While unbranched amylose treated with iodine shows a blue staining, amylopectine exhibits a reddish purple staining. In amylopectin-containing polyacrylamide gels which turn reddish purple when treated with iodine, the color of the gel tends to turn into blue at positions where a debranching activity is localized, since the branchings of the purple-staining amylopectin are dissolved by the debranching enzyme.

Alternatively, the debranching enzyme activity may be shown by means of the DNSS test (see Ludwig et al., Plant Physiol. 74 (1984), 856–861).

The nucleic acid molecules of the invention may be any desired nucleic acid molecules, in particular DNA or RNA molecules, such as cDNA, genomic DNA, mRNA etc. They may be naturally occurring molecules or they may be produced by means of recombinant DNA or chemical techniques.

The nucleic acid molecules according to the present invention encode a so far unknown protein from maize with the enzymatic activity of a debranching enzyme. So far only one locus encoding a protein with debranching enzyme activity has been described for maize (James et al., loc. cit.). There was no indication in the prior art that further debranching-enzyme-encoding genes exist in maize. Homology comparisons of the nucleic acid molecules of the invention with those described in James et al. (loc. cit.) have shown that these sequences do not exhibit any significant homology and would not hybridize to each other. Thus, the molecules of the invention encode a novel type of debranching enzymes from maize. By means of these molecules it is now possible to specifically interfere with the starch metabolism of maize and other starch-storing plants and thus to enable the synthesis of a starch modified in its chemical or physical properties. This may be carried out by over-expressing the nucleic acid molecules of the invention in any desired, preferably starch-storing plants or by reducing the debranching enzyme activity in maize plants by making use of the nucleic acid sequences of the invention, for example by antisense, ribozyme or co suppression effects.

Furthermore, the present invention relates to nucleic acid molecules with a length of at least 15 base pairs, which specifically hybridize to the nucleic acid molecules of the invention. In this context, specifically hybridizing means that these molecules hybridize to nucleic acid molecules encoding the novel debranching enzymes from maize, however, not to nucleic acid molecules encoding other proteins. In this regard, hybridizing preferably means hybridization under stringent conditions (see above). The invention particularly relates to such nucleic acid molecules that hybridize to transcripts of the nucleic acid molecules of the invention, thereby preventing their translation. These are preferably RNA molecules complementary to the transcripts.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and translation in prokaryotic and eukaryotic cells.

In a further embodiment the invention relates to host cells, in particular prokaryotic or eukaryotic cells, which have been transformed by an above-mentioned nucleic acid molecule of the invention or by a vector of the invention, as well as to cells derived from such transformed cells and containing the nucleic acid molecules or vectors of the invention. The host cells may be bacterial or fungal cells, as well as plant or animal cells.

The invention also relates to proteins with the biological activity of a debranching enzyme from maize which are encoded by the nucleic acid molecules of the invention, or to biologically active fragments thereof.

Furthermore, the present invention relates to methods for the production of a plant protein with the biological activity of a debranching enzyme from maize or a biologically active fragment thereof, wherein host cells of the invention are cultivated under suitable conditions and wherein the protein is isolated from the culture, i.e. from the cultivated cells and/or the culture medium.

By the provision of the nucleic acid molecules according to the present invention it is now possible to modify plant cells by means of recombinant DNA techniques in such a way that they exhibit a novel or increased debranching enzyme activity from maize when compared to wildtype cells, i.e. corresponding untransformed cells. Maize cells or maize plants may particularly be modified in such a way that they exhibit a reduced debranching enzyme activity when compared to wildtype cells or plants.

Thus, in a preferred embodiment the host cells of the invention are transgenic plant cells which due to the presence and expression of an introduced nucleic acid molecule of the invention either exhibit a novel or an increased debranching enzyme activity when compared to untransformed cells. Such transgenic plant cells differ from untransformed cells in that the introduced nucleic acid molecule is either heterologous to the transformed cell, i.e. derived from a cell with a different genomic background, or in that the introduced nucleic acid molecule, if it is homologous to transformed plant species, is localized at a position in the genome where it does not naturally occur in non-transformed cells. The introduced nucleic acid molecule may either be subjected to the control of a natural promoter or be linked with regulatory elements of foreign genes.

Transgenic plants containing the above-described transgenic plant cells are also the subject matter of the present invention.

The plant which is transformed with the nucleic acid molecules of the invention and in which a debranching enzyme from maize is synthesized due to the introduction of such a molecule may principally be any desired kind of plant. It is preferably a monocotyledonous or dicotyledonous useful plant, in particular a starch storing plant, such as cereals, Leguminosae, potatoes or cassava.

The cereals are in particular monocotyledonous plants belonging to the Poales order, in particular of the family of the Poaceae. Examples thereof are plants belonging to the genuses Avena (oats), Triticum (wheat), Secale (rye), Hordeum (barley), Oryza (rice), Panicum, Pennisetum, Setaria, Sorghum (millet), Zea (maize) etc., whereby plants from the *Zea mays* species (maize) are particularly preferred. Starch-storing Leguminosae are e.g. some types of the genus Pisum (e.g. *Pisum sativum*), Vicia (e.g. *Vicia faba*), Cicer (e.g. *Cicer arietinum*), Lens (e.g. *Lens culinaris*), Phaseolus (e.g. *Phaseolus vulgaris* and *Phaseolus coccineus*), etc.

The expression of a novel or additional debranching enzyme activity from maize in the transgenic plant cells and plants of the invention influences the degree of branching of the amylopectin synthesized in the cells and plants. Therefore, a starch synthesized in these plants exhibits modified physical and/or chemical properties when compared to starch from wildtype plants. Thus, the invention also relates to the starch obtained from the transgenic plant cells and plants.

Furthermore, the present invention relates to propagation material of the transgenic plants of the invention, such as seeds, fruits, cuttings, tubers, rootstocks etc., wherein this propagation material contains the above-described transgenic plant cells. In the case of maize plants the propagation material are preferably maize kernels.

Furthermore, the present invention relates to transgenic plant cells from maize in which the activity of the debranching enzyme of the invention is reduced due to the inhibition of the transcription or translation of endogeneous nucleic acid molecules encoding a debranching enzyme of the invention. This is preferably achieved by expressing a nucleic acid molecule of the invention or a part thereof in the corresponding plant cells in antisense orientation and by the fact that due to the antisense effect the described debranching enzyme activity is reduced. A further possibility in order to reduce the debranching enzyme activity in plant cells is to express suitable ribozymes that specifically cleave transcripts of the DNA molecules of the invention. The production of such ribozymes by means of the DNA molecules of the invention is known to the skilled person. It is also possible to express molecules which exert an antisense effect in combination with a ribozyme effect. Alternatively, the debranching enzyme activity in the plant cells may be reduced by means of a co suppression effect. The method is known to the skilled person and has e.g. been described in Jorgensen (Trends Biotechnol. 8 (1990), 340–344), Niebel et al. (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al. (Mol. Gen. Genet. 248 (1995, 311–317), de Borne et al. (Mol. Gen. Genet. 243 (1994), 613–621) and other sources.

The invention further relates to transgenic maize plants containing the above-described transgenic plant cells with reduced debranching enzyme activity.

When compared to non-transformed plants, the amylopectin starch of the transgenic cells and plants exhibits a modified degree of branching due to the reduced debranching enzyme activity. Therefore, the modified starch obtainable from the transgenic cells or plants is also the subject matter of the present invention.

The invention also relates to propagation material of the above-described transgenic plants, in particular to seeds, whereby said material contains the above-mentioned transgenic plant cells.

Transgenic plant cells forming an amylopectin starch with a modified degree of branching in comparison to amylopectin starch synthesized in wildtype plants due to the expression of a novel or additional debranching enzyme activity, may for example be produced by a method comprising the following steps:
(a) Production of an expression cassette comprising the following DNA sequences:
   (i) a promoter ensuring the transcription in plant cells;
   (ii) at least one nucleic acid sequence of the invention which encodes a protein with the enzymatic activity of a debranching enzyme or a biologically active fragment thereof and which is coupled to the 3'-end of the promoter in sense-orientation; and
   (iii) optionally, a termination signal for the termination of transcription and the addition of a poly-A-tail to the developing transcript, which is coupled to the 3'-end of the coding region; and
(b) transforming plant cells with the expression cassette produced in step (a).

Transgenic maize plant cells forming an amylopectin starch with a reduced degree of branching in comparison to amylopectin starch synthesized in wildtype plants due to the reduction of the described debranching enzyme activity, may for example be produced by a method comprising the following steps:
(a) Production of an expression cassette comprising the following DNA sequences:
   (i) a promoter ensuring the transcription in plant cells;
   (ii) at least one nucleic acid sequence of the invention which encodes a protein with the enzymatic activity of a debranching enzyme or a biologically active part thereof and which is coupled to the 3'-end of the promoter in antisense-orientation; and
   (iii) optionally, a termination signal for the termination of transcription and the addition of a poly-A-tail to the developing transcript, which is coupled to the 3'-end of the coding region; and
(b) transforming plant cells with the expression cassette produced in step (a).

Basically every promoter functional in the plants selected for transformation may be used as the promoter mentioned under (i). The promoter may be homologous or heterologous with respect to the used plant species. Use may, for example, be made of the 35S promoter of the cauliflower mosaic virus (Odell et al., Nature 313 (1985), 810–812) which ensures a constitutive expression in all plant tissues and also of the promoter construct described in WO/9401571. Another example are the promoters of the polyubiquitin genes from maize (Christensen et al., Plant Mol. Biol. 18 (1992) 675–689). However, use may also be made of promoters which are only activated at a point of time determined by exogeneous factors (such as in WO/9307279). In this regard, promoters of heat-shock proteins allowing for simple induction may be of particular interest. Furthermore, promoters may be used that lead to the expression of downstream sequences in a particular tissue of the plant (see e.g. Stockhaus et al., EMBO J. 8 (1989), 2245–2251). Promoters which are active in the starch-storing parts of the plant to be transformed are preferably used. In the case of maize these parts are the maize kernels, in the case of potatoes the tubers. In order to overexpress the nucleic acid molecules of the invention in potatoes, the tuber-specific B33-promoter (Rocha-Sosa et al., EMBO J. 8 (1989), 23–29) may for example be used.

Seed-specific promoters have already been described for various plant species, such as the USP promoter from *Vicia faba* which ensures a seed-specific expression in *V. faba* and other plants (Fiedler et al., Plant Mol. Biol. 22 (1993), 669–679; Bäumlein et al., Mol. Gen. Genet. 225 (1991), 459467). In the case of maize, for example, promoters of the zein genes ensure a specific expression within the endosperm of the maize kernels (Pedersen et al., Cell 29 (1982), 1015–1026; Quattrocchio et al., Plant Mol. Biol. 15 (1990), 81–93).

In the case that the nucleic acid sequence mentioned under process step (a)(ii), which encodes a protein with the enzymatic activity of a debranching enzyme from maize, is linked to the promoter in sense-orientation, this nucleic acid sequence may be of native or homologous origin as well as of foreign or heterologous origin with respect to the plant species to be transformed, i.e. maize plants as well as any desired other plants (preferably the above-mentioned, starch-storing plants) may be transformed with the described expression cassette.

The synthesized protein may in principle be located in any desired compartment within the plant cell. Plant debranching enzymes are generally located within the plastids and therefore possess a signal sequence for the translocation into these organelles. In order to achieve localization within another compartment, the DNA sequence encoding this signal sequence must be deleted and the coding region has to be linked to DNA sequences which ensure localization in the respective compartment. Such sequences are known (see e.g. Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

In case that the nucleic acid sequence mentioned under process step (a)(ii), which encodes a protein from maize with the enzymatic activity of a debranching enzyme, is linked to the promoter in antisense-orientation, it is preferably a nucleic acid sequence of homologous origin with respect to the plant species to be transformed. However, also nucleic acid sequences may be used which exhibit a high degree of homology to endogeneously present debranching enzyme genes, in particular homologies of more than 80%, preferably homologies of between 90% and 100% and most preferably homologies of more than 95%.

Sequences with a minimum length of 15 bp may be used. Even when using shorter sequences, an inhibiting effect cannot be excluded. Longer sequences ranging between 100 to 500 base pairs are preferably used; for an efficient antisense inhibition, sequences with a length of more than 500 base pairs are used. Usually, use is made of sequences that are shorter than 5000 base pairs, preferably sequences that are shorter than 2500 base pairs.

Termination signals for the transcription in plant cells are described and may be interchanged as desired. For example, use can be made of the termination sequence of the octopin-synthase gene from *Agrobacterium tumefaciens*.

The transfer of the expression cassette constructed according to process step (a) is preferably carried out by using plasmids, in particular by means of plasmids ensuring a stable integration of the expression cassette into the plant genome.

The above-described method for overexpressing a novel debranching enzyme from maize may principally be used for all plant species. In this context, monocotyledonous and dicotyledonous plants and in particular the above-mentioned starch-storing plants are of interest. The above-described method for reducing the debranching enzyme activity is preferably used for monocotyledonous plants, in particular for maize.

Due to the introduction of an expression cassette constructed according to the above-described methods, an RNA is formed within the transformed plant cells. If the nucleic acid sequence encoding a debranching enzyme from maize is linked to the promoter in sense-orientation in the expression cassette, an mRNA is synthesized which may serve as a matrix for the synthesis of an additional or novel debranching enzyme from maize in the plant cells. As a consequence thereof, these cells exhibit an activity or, as the case may be, increased activity of the debranching enzyme from maize, which leads to a modification of the degree of branching of the amylopectin formed in the cells. Thereby, a starch is made accessible which in comparison to naturally occuring starch is characterized by a more clearly ordered structure as well as by an increased homogeneity. This may, among other things, favorably influence the film forming properties.

If, however, the nucleic acid sequence encoding a debranching enzyme from maize is linked to the promoter in antisense-orientation, an antisense-RNA is synthesized within the transgenic plant cells inhibiting the expression of endogeneous debranching enzyme genes. As a consequence, these cells exhibit a reduced activity of the novel debranching enzyme from maize, which leads to the synthesis of a modified starch. By means of the antisense technique it is possible to produce plants in which the expression of an endogeneous debranching enzyme gene in maize is inhibited to different degrees within the range of 0% to 100%. This enables in particular the production of maize plants synthesizing amylopectin starch with most various variations of the degree of branching. This constitutes an advantage with regard to conventional breeding and mutagenesis techniques in which a lot of time and costs are required in order to provide such a variety. Highly branched amylopectin has a particularly large surface and is therefore particularly suitable as a copolymer. A high degree of branching furthermore leads to an improvement of the amylopectin's solubility in water. This property is very advantageous for certain technical applications.

Maize is particularly suitable for the production of modified amylopectin by using the nucleic acid molecules of the invention encoding debranching enzymes. The application of the invention is, however, not limited to this plant species. Any desired other plant species may be used for overexpression.

The modified starch synthesized in the transgenic plants may be isolated from the plants or from the plant cells by means of conventional methods and may be used for the production of foodstuffs and industrial products after purification.

The starch according to the invention can be modified by the person skilled in the art by known methods and can be used in modified or unmodified form for different uses in the food or non-food industry.

Basically, the uses of starch can be subdivided into two major fields. One field comprises the hydrolysis products of starch and the so-called native starches. The hydrolysis products essentially comprise glucose and glucans components obtained by enzymatic or chemical processes. They can be used for further processes, such as fermentation and chemical modifications. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The use of the so-called native starch which is used because of its polymer structure can be subdivided into two further areas:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

2. Use in Non-foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and Cardboard Industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textiles and Textile Care Products

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building Industry

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use in Plant Protectives and Fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processing of Ore and Coal Slurry

Furthermore, the starch may be used as a flocculant in the processing of ore and coal slurry.

2.10 Additive for Casing Materials

Another field of application is the use as an additive to process materials in casting. For various casting processes cores produced from sands mixed with binding agents are needed. Nowadays, the most commonly used binding agent is bentonite mixed with modified starches, mostly swelling starches. The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Rubber Industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of Leather Substitutes

Another field of application for the modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the novel starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

What is decisive for the use of the novel starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art.

These are particularly modifications by means of
heat treatment
acid treatment
oxidation and
esterification
leading to the formation of phosphate, nitrate, sulfate, xanthate, acetate and citrate starches. Other organic acids may also be used for the esterification:
formation of starch ethers
starch alkyl ether, O-allyl ether, hydroxylalkyl ether, O-carboxylmethyl ether, N-containing starch ethers, P-containing starch ethers and S-containing starch ethers.
formation of branched starches
formation of starch graft polymers.

In principle, the nucleic acid molecules of the invention may also be used in order to produce plants in which the activity of the debranching enzyme of the invention is elevated or reduced and in which at the same time the activities of other enzymes involved in the starch biosynthesis are modified. In this regard, all kinds of combinations and permutations are conceivable. For example, nucleic acid molecules encoding a protein of the invention, or corresponding antisense-constructs may be introduced into plant cells in which the synthesis of endogenous GBSS I-, SSS I-, II- or GBSS II-proteins or of the su-gene is already inhibited due to an antisense-effect or a mutation, or in which the synthesis of the branching enzyme is inhibited (as described e.g. WO92/14827 or in connection with the ae mutant (Shannon and Garwood, 1984, in Whistler, BeMiller and Paschall, Starch: Chemistry and Technology, Academic Press, London, $2^{nd}$ edition (1984) 25–86)).

If the inhibition of the synthesis of several debranching enzymes in transformed plants is to be achieved, DNA molecules can be used for transformation, which at the same time contain several regions in antisense-orientation encoding the respective debranching enzymes and which are controlled by a suitable promoter, or which encode a corresponding co suppression RNA or a corresponding ribozyme. In such constructs, each sequence may alternatively be controlled by its own promoter or else the sequences may be transcribed as a fusion from a common promoter. The last alternative will generally be preferred as in this case the synthesis of the respective proteins should be inhibited to approximately the same extent.

Furthermore, it is possible to construct DNA molecules in which, apart from DNA sequences encoding debranching enzymes, other DNA sequences are present encoding other proteins involved in the starch synthesis or modification. These may encode an antisense RNA, a corresponding ribozyme or a cosupression RNA. Again, the sequences may be connected up in series and be transcribed from a common promoter or each may be transcribed by a promoter of its own. There is no upper limit for the number of antisense fragments transcribed from one promoter in such a DNA molecule. The resulting transcript, however, should usually not be longer than 20 kb, preferably not longer than 5 kb.

Coding regions which are located downstream of a suitable promoter in such DNA molecules in combination with other coding regions may be derived from DNA sequences encoding the following proteins: granule-bound starch synthases (GBSS I and II), other soluble starch synthases (SSS I and II), branching enzymes, debranching enzymes, disproportionizing enzymes and starch phosphorylases. This enumeration merely serves as an example. The use of other DNA sequences within the framework of such a combination is also conceivable.

By means of such constructs it is possible to inhibit the synthesis of several enzymes at the same time within the plant cells transformed with these constructs.

Furthermore, the constructs may be introduced into classical mutants which are defective for one or more genes of the starch biosynthesis (Shannon and Garwood, loc. cit.). These defects may be related to the following proteins: granule-bound (GBSS I and II) and soluble starch synthases (e.g. SSS I and II), branching enzymes (BE I and II), debranching enzymes (su-locus), disproportionizing enzymes and starch phosphorylases. Again, this enumeration merely serves as an example.

In order to prepare the introduction of foreign genes into higher plants a high number of cloning vectors are at disposal, containing a replication signal for E.coli and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of E.coli cells. Transformed E.coli cells are cultivated in a suitable medium and subsequently harvested and lysed. The plasmid is recovered. As an analyzing method for the characterization of the obtained plasmid DNA use is generally made of restriction analysis, gel electrophoresis and other biochemico-molecular biological methods. After each manipulation the plasmid DNA may be cleaved and the obtained DNA fragments may be linked to other DNA sequences. Each plasmid DNA may be cloned into the same or in other plasmids.

In order to introduce DNA into a plant host cell a wide range of techniques are at disposal. These techniques comprise the transformation of plant cells with T-DNA by using Agrobacterium tumefaciens or Agrobacterium rhizogenes as transformation medium, the fusion of protoplasts, the injection and the electroporation of DNA, the introduction of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present. Depending on the method of introducing desired genes into the plant cell, further DNA sequences may be necessary. If the Ti- or Ri-plasmid is used e.g. for the transformation of the plant cell, at least the right border, more frequently, however, the right and left border of the Ti- and Ri-plasmid T-DNA should be connected to the foreign gene to be introduced as a flanking region.

If Agrobacteria are used for the transformation, the DNA which is to be integrated must be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to Agrobacterium tumefaciens (conjugation). Binary vectors may replicate in E.coli as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 146 and An et al. EMBO J. 4 (1985), 277–287.

For transferring the DNA into the plant cells, plant explants may suitably be co-cultivated with Agrobacterium tumefaciens or Agrobacterium rhizogenes. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the introduced DNA is present or not. Other possibilities in order to introduce foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Pühler, P. Stadler, editors), Vol. 2, 627459, VCH Weinheim-New York-Basel-Cambridge).

Whereas the transformation of dicotyledonous plants via Ti-plasmid vector systems by means of Agrobacterium tumefaciens is well established, more recent studies indicate that also monocotyledonous plants may be suitable for the transformation by means of vectors based on Agrobacterium (Chan et al., Plant Mol. Biol. 22 (1993), 491–506; Hiei et al., Plant J. 6 (1994), 271–282, Deng et al., Science in China 33 (1990), 28–34; Wilmink et al, Plant Cell Reports 11 (1992), 76–80; May et al., Bio/Technology 13 (1995), 486492; Conner and Domisse; Int. J. Plant Sci. 153 (1992), 550–555; Ritchie et al., Transgenic Res. 2 (1993), 252–265).

Alternative Systems for the transformation of monocotyledonous plants are the transformation by means of a biolistic approach (Wan and Lemaux, Plant Physiol. 104 (1994), 37–48; Vasil et al., Bio/Technology 11 (1993), 1553–1558; Ritala et al., Plant Mol. Biol. 24 (1994), 317–325; Spencer et al., Theor. Appl. Gent. 79 (1990), 625–631), protoplast transformation, the electroporation of partially permeabilized cells, the introduction of DNA by means of glass fibers.

There are various references in the relevant literature dealing specifically with the transformation of maize (cf. e.g. WO95/06128, EP 0 513 849; EP 0 465 875; Fromm et al., Biotechnology 8 (1990), 833–844; Gordon-Kamm et al., Plant Cell 2 (1990), 603–618; Koziel et al., Biotechnology 11 (1993), 194–200). In EP 292 435 a method is described by means of which fertile plants may be obtained starting from mucousless, friable granulous maize callus. In this context it was furthermore observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity.

Prioli and Söndahl (Bio/Technology 7 (1989), 589) have described how to regenerate and to obtain fertile plants from maize protoplasts of the Cateto maize inbreed line Cat 100-1. The authors assume that the regeneration of protoplast to fertile plants depends on a number of various factors such as the genotype, the physiological state of the donor-cell and the cultivation conditions. The successful transformation of other cereals has by now also been described, such as for barley (Wan and Lemaux, loc. cit.; Ritala et al., loc. cit.) and for wheat (Nehra et al., Plant J. 5 (1994), 285–297).

Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties. Seeds may be obtained from the plant cells.

Two or more generations should be grown in order to ensure whether the phenotypic feature is kept stably and whether it is transferred. Furthermore, seeds should be harvested in order to ensure that the corresponding phenotype or other properties will remain.

Furthermore, the present invention relates to the use of the nucleic acid molecules of the invention for producing plants synthesizing an amylopectin starch with a modified degree of branching in comparison to wildtype plants.

A further subject matter of the present invention is the use of the nucleic acid molecules of the invention or parts thereof or, as the case may be, of the reverse complements thereof in order to identify and isolate from plants and other organisms homologous molecules encoding proteins with the enzymatic activity of a debranching enzyme or fragments of such proteins. For the term "homology", please refer to the above definition.

The examples illustrate the invention.

Media and Solutions Used:

Protoplast Isolation Medium (100 ml)

| Cellulase Onozuka R S (Meiji Seika, Japan) | 800 mg |
|---|---|
| Pectolyase Y 23 | 40 mg |
| $KNO_3$ | 200 mg |
| $KH_2PO_4$ | 136 mg |
| $K_2HPO_4$ | 47 mg |
| $CaCl_2\ 2H_2O$ | 147 mg |
| $MgSO_4\ 7H_2O$ | 250 mg |
| Bovine serum albumine (BSA) | 20 mg |

-continued

| Glucose | 4000 mg |
|---|---|
| Fructose | 4000 mg |
| Sucrose | 1000 mg |
| pH | 5.8 |
| Osmolarity | 660 mosm. |

Protoplast Washing Solution 1: like protoplast isolating solution, but without cellulase, pectolyase and BSA Transformation Buffers:

| a) Glucose | 0.5 M |
|---|---|
| MES | 0.1% |
| $MgCl_2\ 6H_2O$ | 25 mM |
| pH | 5.8 |
| adjust to 600 mosm. | |

| b) PEG 6000-solution | |
|---|---|
| Glucose | 0.5 M |
| $MgCl_2\ 6H_2O$ | 100 mM |
| Hepes | 20 mM |
| pH | 6.5 |

PEG 6000 is added to the buffer described in b) immediately prior to the use of the solution (40% w/v PEG). The solution is filtered through a 0.45 μm sterile filter.

W5 Solution

| $CaCl_2$ | 125 mM |
|---|---|
| NaCl | 150 mM |
| KCl | 5 mM |
| Glucose | 50 mM |

Protoplast Culture Medium (indicated in mg/l)

| $KNO_3$ | 3000 |
|---|---|
| $(NH_4)_2SO_4$ | 500 |
| $MgSO_4\ 7H_2)$ | 350 |
| $KH_2PO_4$ | 400 |
| $CaCl_2\ 2H_2O$ | 300 |

Fe-EDTA and trace elements as in the Murashige-Skoog medium (Physiol. Plant, 15 (1962), 473).

| m-inosite | 100 |
|---|---|
| Thiamine HCl | 1.0 |
| Nicotine acid amide | 0.5 |
| Pyridoxine HCl | 0.5 |
| Glycine | 2.0 |
| Glucuronic acid | 750 |
| Galacturonic acid | 750 |
| Galactose | 500 |
| Maltose | 500 |
| Glucose | 36,000 |
| Fructose | 36,000 |
| Sucrose | 30,000 |
| Asparagine | 500 |
| Glutamine | 100 |
| Proline | 300 |

| | |
|---|---|
| Caseinhydrolysate | 500 |
| 2,4 dichlorophenoxy acetic acid (2,4-D) | 0.5 |
| pH | 5.8 |
| Osmolarity | 600 mosm. |

In the examples the following methods were used:

1. Cloning Methods

For cloning in *E.coli* the vector pBluescript II SK (Stratagene) was used.

2. Bacterial Strains

For the Bluescript vector and for the pUSP constructs use was made of the *E.coli* strain DH5α (Bethesda Research Laboratories, Gaithersburgh, USA). The *E.coli* strain XL1-Blue was used for in vivo excision.

3. Transformation of Maize (a) Production of protoplasts of the cell line DSM 6009

Protoplast isolation

2–4 days, preferably 3 days after the last change of medium in a protoplast suspension culture the liquid medium is pumped off and the remaining cells are washed in 50 ml protoplast washirg solution 1 and sucked dry once more. 10 ml protoplast isolation medium are added to 2 g of harvested cell mass. The resuspended cells and cell aggregates are incubated at 27±2° C. for 4 to 6 hours in the darkness, while shaking it slightly (at 30 to 40 rpm).

Protoplast purification

As soon as the release of at least 1 million protoplasts/ml has taken place (microscopic inspection), the suspension is sifted through a stainless steel or nylon sieve with a mesh size of 200 or 45 μm. The combination of a 100 μm and a 60 μm sieve allows for separating the cell aggregates just as well. The protoplast-containing filtrate is examined microscopically. It usually contains 98–99% protoplasts. The rest are undigested single cells. Protoplast preparations with such a degree of purity are used for transformation experiments without additional gradient centrifugation. The protoplasts are sedimented by means of centrifugation (100 UpM in the swing-out rotor (100×g, 3 minutes)). The supernatant is abandoned and the protoplasts are resuspended in washing solution 1. The centrifugation is repeated and the protoplasts are subsequently resuspended in the transformation buffer.

(b) Protoplast transformation

The protoplasts resuspended in the transformation buffer are filled in 10 ml portions into 50 ml poly-allomer tubes at a titer of 0.5–1×10$^6$ protoplasts/ml. The DNA used for transformation is dissolved in Tris-EDTA (TE) buffer solution. 20 μg plasmid DNA is added to each ml protoplast suspension. A plasmid which provides for resistance to phosphinotricine is used as vector (cf. e.g. EP 0 513 849). After the addition of DNA the protoplast suspension is carefully shaken in order to homogenously distribute the DNA in the solution. Immediately afterwards 5 ml PEG solution is added in drops.

By carefully shaking the tubes the PEG solution is distributed homogeneously. Afterwards further 5 ml of PEG solution are added and the homogenous mixing is repeated. The protoplasts remain in the PEG solution for 20 minutes at ±2° C. Afterwards the protoplasts are sedimented by centrifuging for 3 minutes (100 g; 1000 Upm). The supernatant is abandoned. The protoplasts are washed in 20 ml W5 solution by careful shaking and are again subjected to centrifugation. Then they are resuspended in 20 ml protoplast culture medium, centrifuged anew and again resuspended in culture medium. The titer is adjusted to 6–8×10$^5$ protoplasts and the protoplasts are cultivated in 3 ml portions in Petri dishes (Ø60 mm, height 15 mm). The Petri dishes are sealed with parafilm and stored in darkness at 25±2° C.

(c) Protoplast culture

During the first 2–3 weeks after the protoplast isolation and transformation the protoplasts are cultivated without adding fresh medium. As soon as the cells regenerated from the protoplasts have developed into cell aggregates with more than 20 to 50 cells, 1 ml of fresh protoplast culture medium, containing sucrose as an osmotic (90 g/l), is added.

(d) Selection of transformed maize cells and plant regeneration

3–10 days after adding fresh medium the cell aggregates developed from the protoplasts may be plated on Agar media with 100 mg/l L-phosphinothricine. N6-medium with the vitamins of the protoplast culture medium, 90 g/l sucrose and 1.0 mg/l 2,4D is as suitable as an analogous medium such as a medium with the macro- and micro-nutritive salts of the MS medium (Murashige and Skoog (1962), see above).

The calli developed from stably transformed protoplasts may grow further on the selective medium. After 3 to 5 weeks, preferably 4 weeks the transgenic calli may be transferred to fresh selection medium which also contains 100 mg/l L-phosphinothricine which, however, no longer contains auxine. Within 3 to 5 weeks approximately 50% of the transgenic maize calli which had integrated the L-phosphinothricine-acetyl-transferase gene into their genome, start to differentiate into plants on this medium in the presence of L-phosphinothricine.

(e) Growing of transgenic regenerative plants

The embryogenical transformed maize tissue is cultivated on hormone-free N6-medium (Chu C.C. et al., Sci. Sin. 16 (1975), 659) in the presence of 5×10$^{-4}$ M L-phosphinothricine. On this medium maize embryos, which express the phosphinothricine-acetyl-transferase gene (PAT gene) in a sufficiently strong manner, develop into plants. Non-transformed embryos or such with only a very weak PAT activity die down. As soon as the leaves of the in-vitro plants have reached a length of 4 to 6 mm, they may be transferred into soil. After washing off the Agar residues at the roots the plants are planted into a mixture of clay, sand, vermiculite and potting soil with the ratio 3:1:1:1 and adapted to the soil culture at 90–100% of relative atmospheric humidity during the first 3 days after planting. The growing is carried out in a climate chamber with a 14 hour light period of approximately 25000 lux at the height of the plant at a day/night temperature of 23±1/17±1° C. The adapted plants are cultivated at an 65±5% atmospheric humidity.

4. Radioactive Marking of DNA Fragments

The radioactive marking of DNA fragments was carried out by means of a DNA-Random Primer Labeling Kits by Boehringer (Germany) according to the manufacturer's instructions.

EXAMPLE 1

Cloning of a cDNA Encoding a Novel Debranching Enzyme from *Zea mays*

In order to isolate cDNA molecules encoding a starch debranching enzyme from maize, a cDNA library was constructed within the vector Lambda ZAPII (Stratagene) starting from polyA+ RNA from maize leaves and packed into phage heads. E.coli cells of the XL1 Blue strain were subsequently infected with the phages containing the cDNA fragments ($1\times10^6$ pfu) and plated on medium in Petri dishes with a densitiy of approximately 30,000 per 75 $cm^2$. After an 8-hour incubation, nitrocellulose membranes were put on the lysed bacteria and removed after one minute. The filters were first incubated in 0.2 M NaOH; 1.5 M NaCl for 2 minutes and then in 0.4 M Tris/HCl pH 7.5 for 2 minutes and finally in 2×SSC for 2 minutes. After drying and fixing the DNA by means of UV crosslinking, the filters were incubated in hybridization buffer for 3 hours at 42° C. before a radioactively labeled probe was added.

As a probe, use was made of a cDNA from potato encoding a debranching enzyme from potato (see SEQ ID No. 3). This cDNA had beforehand been isolated by means of degenerated oligonucleotides which had been derived from the partial amino acid sequence of a debranching enzyme from potato.

The hybridization was carried out in 2×SSC, 10×Dehnhardt's solution; 50 mM $Na_2HPO_4$, pH 7.2; 0.2% SDS; 5 mM EDTA and 250 µg/ml denatured herring sperm DNA at 48° C.

Hybridizing phage clones were singled out and further purified by means of standard methods. By means of in vivo excision E.coli clones were derived from positive phage clones. The E.coli clones contained a double-stranded pBluescript plasmid with the respective cDNA insertions. After examining the size and the restriction pattern of the insertion, plasmid DNA was isolated from suitable clones. pREM-53, a plasmid isolated in such a way, contained an insertion of 1195 bp.

EXAMPLE 2

Sequence Analysis of the cDNA Insert of the pREM-53 Plasmid

In the case of the plasmid pREM-53, which was isolated as described in Example 1, the nucleotide sequence of the cDNA insert was determined in a standard routine by means of the didesoxynucleotide-method (Sanger et al., Proc. Nati. Acad. Sci. USA 74 (1977), 5463–5467). The insert has a length of 1995 bp. The nucleotide sequence and the corresponding amino acid sequence are indicated under Seq ID No. 1. Homology comparisons showed that the encoded protein was a novel debranching enzyme from maize.

The nucleotide sequence depicted under SEQ ID No. 1 represents a partial cDNA encoding a so far unknown debranching enzyme from maize. By means of this sequence it is possible to isolate a complete cDNA sequence or a genomic sequence from suitable cDNA or genomic libraries by means of standard techniques.

What is claimed is:

1. An isolated nucleic acid molecule comprising a nucleic acid sequence encoding a protein with the enzymatic activity of a debranching enzyme, wherein the nucleic acid sequence is selected from the group consisting of:
   (a) a nucleic acid sequence encoding a protein comprising the amino acid sequence of SEQ ID NO: 2;
   (b) a nucleic acid sequence that is SEQ ID NO: 1;
   (c) a nucleic acid molecule that has more than 90% sequence identity to the coding region of (a) or (b);
   (d) a fragment of the nucleic acid sequence of (a), (b) or (c), wherein the fragment encodes a protein which has the enzymatic activity of a debranching enzyme; and
   (e) a nucleic acid sequence that deviates from (a), (b), (c) or (d) due to the degeneracy of the genetic code.

2. The isolated nucleic acid molecule according to claim 1, wherein the nucleic acid molecule is a cDNA molecule.

3. The isolated nucleic acid molecule according to claim 1, wherein the nucleic acid sequence is the coding region of SEQ ID NO: 1.

4. The isolated nucleic acid molecule according to claim 1, wherein the nucleic acid sequence encodes a protein comprising the amino acid sequence of SEQ ID NO: 2.

5. The isolated nucleic acid molecule according to claim 1, wherein the nucleic acid molecule is an RNA molecule.

6. A vector comprising the nucleic acid molecule according to any one of claims 1, 2, or 3–5.

7. The vector according to claim 6, wherein said nucleic acid molecule is linked in sense-orientation to regulatory elements that enable transcription of the nucleic acid molecule and translation of the debranching enzyme encoded therein in a prokaryotic or a eukaryotic cell.

8. A host cell comprising a heterologous nucleic acid molecule according to any one of claims 1, 2, or 3–5 or comprising a vector comprising said nucleic acid molecule, or a cell that is derived from the host cell.

9. A method for producing a protein with the enzymatic activity of a debranching enzyme comprising the steps of cultivating the host cell according to claim 8 under suitable conditions to produce the protein and recovering the protein produced by the culture.

10. A transgenic plant cell comprising a heterologous nucleic acid molecule according to any one of claims 1, 2, or 3–5 or comprising a vector comprising the nucleic acid molecule, wherein the nucleic acid molecule is placed under the control of regulatory elements to allow the transcription of a translatable MRNA in plant cells.

11. A transgenic plant comprising the transgenic plant cell according to claim 10.

12. The transgenic plant cell according to claim 11, wherein the plant is a starch-storing plant.

13. The transgenic plant according to claim 12, wherein the starch-storing plant is selected from the group consisting of cereals, leguminosae, potatoes and cassava.

14. The transgenic plant according to claim 13, wherein the cereal plant is a maize plant.

15. A propagation material of a plant comprising the plant cell according to claim 10.

16. An isolated nucleic acid molecule comprising a nucleic acid sequence, wherein said isolated nucleic acid molecule, when introduced into a plant cell, has a cosuppression effect on the expression of a debranching enzyme, wherein the nucleic acid sequence is selected from the group consisting of:

(a) a nucleic acid sequence encoding a protein comprising the amino acid sequence of SEQ ID NO:2;

(b) a nucleic acid sequence that is the coding region of SEQ ID NO:1;

(c) a nucleic acid sequence that has at least 90% sequence identity to (a) or (b);

(d) a part of the nucleic acid sequence of (a), (b) or (c), wherein the part is sufficient to reduce the activity of debranching enzyme; and (e) the complementary strand of the nucleic acid sequence of (a), (b), (c) or (d).

17. The isolated nucleic acid molecule of claim 16, wherein the nucleic acid sequence has greater than 95% sequence identity to the coding region of SEQ ID NO: 1.

18. A transgenic plant cell, wherein the activity of the debranching enzyme is reduced when compared to untransformed cells due to expression of a co suppression RNA from the nucleic acid molecule according to claim 16 or 17.

19. A transgenic plant comprising a plant cell according to claim 18.

20. The transgenic plant according to claim 19, wherein the plant is a maize plant.

21. A propagation material of a plant comprising the plant cell according to claim 18.

22. A vector comprising the nucleic acid molecule according to claim 16 or 17.

23. A host cell comprising the heterologous nucleic acid molecule according to claim 16 or 17 or comprising a vector comprising said nucleic acid molecule.

24. A transgenic plant cell that exhibits increased activity of a debranching enzyme when compared to untransformed cells, and wherein the transgenic plant cell comprises a recombinant molecule integrated into its genome, wherein said recombinant molecule comprises:

a) a promoter active in plant cells;

b) the nucleic acid molecule according to any one of claims 1, 2, or 3–5, wherein the nucleic acid molecule is linked to the promoter in sense-orientation; and c) optionally, a termination signal for the termination of transcription and the addition of a poly-A tail to the developing transcript.

25. A transgenic plant comprising the plant cell according to claim 24.

26. A propagation material of the transgenic plant according to claim 25.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1993 base pairs
      (B) TYPE: nucleotide
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: Zea mays
      (F) TISSUE TYPE: Blattgewebe (ix) FEATURE:
      (A) NAME/KEY: CDS
      (B) LOCATION:1..1675

(xi) SEQUENCE DESCRIPTION: SEQ ID NO: 1:

```
GGC ACG AGG TCA AAA CTC CCT CCA GGG TCA GAT TTG CAA CAA GCT GCA        48
Gly Thr Arg Ser Lys Leu Pro Pro Gly Ser Asp Leu Gln Gln Ala Ala
 1               5                  10                  15

ATT GTG GCT ATT CAG GAA GAG GAC CCT TAT AAT TGG GGG TAT AAC CCT        96
Ile Val Ala Ile Gln Glu Glu Asp Pro Tyr Asn Trp Gly Tyr Asn Pro
                20                  25                  30

GTG GTT TGG GGC GTT CCA AAA GGA AGC TAT GCA AGT AAC CCA GAT GGT       144
Val Val Trp Gly Val Pro Lys Gly Ser Tyr Ala Ser Asn Pro Asp Gly
            35                  40                  45
```

```
CCA AGT CGT ATC ATT GAG TAC CGG CTG ATG GTG CAG GCC TTG AAT CGC    192
Pro Ser Arg Ile Ile Glu Tyr Arg Leu Met Val Gln Ala Leu Asn Arg
         50                  55                  60

TTA GGT CTT CGA GTT GTC ATG GAT GTT GTA TAC AAT CAT CTA TAC TCA    240
Leu Gly Leu Arg Val Val Met Asp Val Val Tyr Asn His Leu Tyr Ser
 65                  70                  75                  80

AGT GGC CCT TTT GCC ATC ACT TCC GTG CTT GAC AAG ATT GTA CCT GGA    288
Ser Gly Pro Phe Ala Ile Thr Ser Val Leu Asp Lys Ile Val Pro Gly
                 85                  90                  95

TAC TAC CTC AGA AGG GAC TCT AAT GGT CAG ACT GAG AAC AGC GCG GCT    336
Tyr Tyr Leu Arg Arg Asp Ser Asn Gly Gln Thr Glu Asn Ser Ala Ala
             100                 105                 110

GTG AAC AAT ACA GCA AGT GAG CAT TTC ATG GTT GAT AGA TTA ATC GTG    384
Val Asn Asn Thr Ala Ser Glu His Phe Met Val Asp Arg Leu Ile Val
         115                 120                 125

GAT GAC CTT CTG AAT TGG GCA GTA AAT TAC AAA GTT GAC GGG TTC AGA    432
Asp Asp Leu Leu Asn Trp Ala Val Asn Tyr Lys Val Asp Gly Phe Arg
     130                 135                 140

TTT GAT CTA ATG GGA CAT ATC ATG AAA AAG ACA ATG ATT AGA GCA AAA    480
Phe Asp Leu Met Gly His Ile Met Lys Lys Thr Met Ile Arg Ala Lys
145                 150                 155                 160

TCG GCT CTT CAA AGC CTT ACA ATT GAT GAA CAT GGA GTA GAT GGT TCA    528
Ser Ala Leu Gln Ser Leu Thr Ile Asp Glu His Gly Val Asp Gly Ser
                 165                 170                 175

AAG ATA TAC TTG TAT GGT GAA GGA TGG AAC TTC GGT GAA GTT GCG GAA    576
Lys Ile Tyr Leu Tyr Gly Glu Gly Trp Asn Phe Gly Glu Val Ala Glu
             180                 185                 190

AAT CAA CGT GGG ATA AAT GGA TCC CAG CTA AAT ATG AGT GGC ACT GGG    624
Asn Gln Arg Gly Ile Asn Gly Ser Gln Leu Asn Met Ser Gly Thr Gly
         195                 200                 205

ATT GGT AGT TTC AAC GAT AGA ATC CGT GAT GCT ATA AAT GGT GGC AGT    672
Ile Gly Ser Phe Asn Asp Arg Ile Arg Asp Ala Ile Asn Gly Gly Ser
     210                 215                 220

CCG TTT GGG AAT CCA CTG CAA CAA GGT TTC TCT ACT GGA TTG TTC TTA    720
Pro Phe Gly Asn Pro Leu Gln Gln Gly Phe Ser Thr Gly Leu Phe Leu
225                 230                 235                 240

GAG CCA AAT GGA TTT TAT CAG GGC AAT GAA ACA GAG ACA AGG CTC ACG    768
Glu Pro Asn Gly Phe Tyr Gln Gly Asn Glu Thr Glu Thr Arg Leu Thr
                 245                 250                 255

CTT GCT ACA TAC GCT GAC CAT ATA CAG ATT GGA TTA GCT GGC AAT TTG    816
Leu Ala Thr Tyr Ala Asp His Ile Gln Ile Gly Leu Ala Gly Asn Leu
             260                 265                 270

AAG GAC TAT GTA GTT ATA TCT CAT ACT GGA GAA GCT AGA AAA GGA TCT    864
Lys Asp Tyr Val Val Ile Ser His Thr Gly Glu Ala Arg Lys Gly Ser
         275                 280                 285

GAA ATT CGC ACC TTC GAT GGC TCA CCA GTT GGC TAT GCT TCA TCC CCT    912
Glu Ile Arg Thr Phe Asp Gly Ser Pro Val Gly Tyr Ala Ser Ser Pro
     290                 295                 300

ATA GAA ACA ATA AAC TAC GCC TCT GCT CAT GAC AAT GAA ACA CTA TTT    960
Ile Glu Thr Ile Asn Tyr Ala Ser Ala His Asp Asn Glu Thr Leu Phe
305                 310                 315                 320

GAT ATT ATT AGT CTA AAG ACT CCG ATG GAC CTC TCA ATT GAC GAG CGA   1008
Asp Ile Ile Ser Leu Lys Thr Pro Met Asp Leu Ser Ile Asp Glu Arg
                 325                 330                 335

TGC AGG ATA AAT CAT TTG TCC ACA AGC ATG ATT GCA TTA TCC CAG GGA   1056
Cys Arg Ile Asn His Leu Ser Thr Ser Met Ile Ala Leu Ser Gln Gly
             340                 345                 350

ATA CCA TTT TTT CAT GCT GGT GAT GAG ATA CTA CGA TCT AAG TCG CTT   1104
Ile Pro Phe Phe His Ala Gly Asp Glu Ile Leu Arg Ser Lys Ser Leu
```

-continued

```
                            355                 360                      365
GAT CGA GAT TCA TAT GAC TCT GGT GAT TGG TTT AAC AAG ATT GAT TTT          1152
Asp Arg Asp Ser Tyr Asp Ser Gly Asp Trp Phe Asn Lys Ile Asp Phe
        370                 375                 380

ACC TAT GAA ACA AAT AAT TGG GGT GTT GGG CTT CCA CCA AGA GAA AAG          1200
Thr Tyr Glu Thr Asn Asn Trp Gly Val Gly Leu Pro Pro Arg Glu Lys
385                 390                 395                 400

AAC GAA GGG AGC TGG CCT TTG ATG AAG CCA AGA TTG GAG AAC CCG TCG          1248
Asn Glu Gly Ser Trp Pro Leu Met Lys Pro Arg Leu Glu Asn Pro Ser
                405                 410                 415

TTC AAA CCT GCA AAA CAT GAC ATT ATT GCT GCC TTA GAC AAA TTT ATT          1296
Phe Lys Pro Ala Lys His Asp Ile Ile Ala Ala Leu Asp Lys Phe Ile
            420                 425                 430

GAT ATC CTC AAG ATC AGA TAC TCA TCA CCT CTC TTT CGC CTA ACT ACA          1344
Asp Ile Leu Lys Ile Arg Tyr Ser Ser Pro Leu Phe Arg Leu Thr Thr
                435                 440                 445

GCA AGT GAT ATT GTG CAA AGG GTT CAC TTT CAC AAC ACA GGG CCC TCC          1392
Ala Ser Asp Ile Val Gln Arg Val His Phe His Asn Thr Gly Pro Ser
        450                 455                 460

TTG GTT CCA GGA GTT ATT GTC ATG AGC ATC GAA GAT GCA CGA AAT GAT          1440
Leu Val Pro Gly Val Ile Val Met Ser Ile Glu Asp Ala Arg Asn Asp
465                 470                 475                 480

AGG CAT GAT ATG GCC CAG ATA GAT GAA ACA TTC TCT TGT GTC GTT ACA          1488
Arg His Asp Met Ala Gln Ile Asp Glu Thr Phe Ser Cys Val Val Thr
                485                 490                 495

GTC TTC AAT GTA TGT CCG TAC GAA GTG TCT ATA GAA ATC CCT GAT CTT          1536
Val Phe Asn Val Cys Pro Tyr Glu Val Ser Ile Glu Ile Pro Asp Leu
            500                 505                 510

GCA TCA CTG CGG CTT CAG TTG CAT CCA GTG CAG GTG AAT TCA TCG GAT          1584
Ala Ser Leu Arg Leu Gln Leu His Pro Val Gln Val Asn Ser Ser Asp
                515                 520                 525

GCG TTA GCC AGG CAG TCT GCG TAC GAC ACC GCC ACA GGT CGA TTC ACC          1632
Ala Leu Ala Arg Gln Ser Ala Tyr Asp Thr Ala Thr Gly Arg Phe Thr
        530                 535                 540

GTG CCG AAA AGG ACA GCA GCA GTG TTC GTG GAA CCC AGG TGC T                1675
Val Pro Lys Arg Thr Ala Ala Val Phe Val Glu Pro Arg Cys
545                 550                 555

GATGGATGCC TTTCGCTAGC GAGCAAGTGC ATTCGGCATC CAAGTCGAAG CAAACGAATG        1735

AAATAAGAGA AGGCCATCGA ATAAAACGAA GTATATAAAT AGATTGAATA AGACGTTGCC        1795

CAAGTTGCCA AGGCACGCTT TGCCATATGT ATGCGTTGAA AAATAAATAA ATAAATAAAT        1855

AAATGATGTT ATAGAGGTAC AAAAGCATTG GAACATTTCT TTATAGAGGT GAACCACCCT        1915

ATTTTCCAGT TTCCATGTGT GAATTGTGAT TAGCATATGT ATGGAATAAT AATATAAATT        1975

AATTTTATGC AAAAAAA                                                       1993
```

(2) INFORMATION FOR SEQ ID NO: 2:

(i) SEQUENCE CHARACTERISTICS:
        (A) LENGTH: 558 amino acids
        (B) TYPE: amino acid
        (D) TOPOLOGY: linear (ii) MOLECULE TYPE: protein (xi) SEQUENCE DESCRIPTION: SEQ ID NO: 2:

```
Gly Thr Arg Ser Lys Leu Pro Pro Gly Ser Asp Leu Gln Gln Ala Ala
 1               5                  10                  15

Ile Val Ala Ile Gln Glu Glu Asp Pro Tyr Asn Trp Gly Tyr Asn Pro
            20                  25                  30
```

```
Val Val Trp Gly Val Pro Lys Gly Ser Tyr Ala Ser Asn Pro Asp Gly
         35                  40                  45

Pro Ser Arg Ile Ile Glu Tyr Arg Leu Met Val Gln Ala Leu Asn Arg
         50                  55                  60

Leu Gly Leu Arg Val Val Met Asp Val Val Tyr Asn His Leu Tyr Ser
 65              70                  75                      80

Ser Gly Pro Phe Ala Ile Thr Ser Val Leu Asp Lys Ile Val Pro Gly
                 85                  90                  95

Tyr Tyr Leu Arg Arg Asp Ser Asn Gly Gln Thr Glu Asn Ser Ala Ala
             100                 105                 110

Val Asn Asn Thr Ala Ser Glu His Phe Met Val Asp Arg Leu Ile Val
             115                 120                 125

Asp Asp Leu Leu Asn Trp Ala Val Asn Tyr Lys Val Asp Gly Phe Arg
             130                 135                 140

Phe Asp Leu Met Gly His Ile Met Lys Lys Thr Met Ile Arg Ala Lys
145                  150                 155                 160

Ser Ala Leu Gln Ser Leu Thr Ile Asp Glu His Gly Val Asp Gly Ser
                 165                 170                 175

Lys Ile Tyr Leu Tyr Gly Glu Gly Trp Asn Phe Gly Glu Val Ala Glu
             180                 185                 190

Asn Gln Arg Gly Ile Asn Gly Ser Gln Leu Asn Met Ser Gly Thr Gly
             195                 200                 205

Ile Gly Ser Phe Asn Asp Arg Ile Arg Asp Ala Ile Asn Gly Gly Ser
             210                 215                 220

Pro Phe Gly Asn Pro Leu Gln Gln Gly Phe Ser Thr Gly Leu Phe Leu
225                  230                 235                 240

Glu Pro Asn Gly Phe Tyr Gln Gly Asn Glu Thr Glu Thr Arg Leu Thr
                 245                 250                 255

Leu Ala Thr Tyr Ala Asp His Ile Gln Ile Gly Leu Ala Gly Asn Leu
             260                 265                 270

Lys Asp Tyr Val Val Ile Ser His Thr Gly Glu Ala Arg Lys Gly Ser
             275                 280                 285

Glu Ile Arg Thr Phe Asp Gly Ser Pro Val Gly Tyr Ala Ser Ser Pro
             290                 295                 300

Ile Glu Thr Ile Asn Tyr Ala Ser Ala His Asp Asn Glu Thr Leu Phe
305                  310                 315                 320

Asp Ile Ile Ser Leu Lys Thr Pro Met Asp Leu Ser Ile Asp Glu Arg
                 325                 330                 335

Cys Arg Ile Asn His Leu Ser Thr Ser Met Ile Ala Leu Ser Gln Gly
             340                 345                 350

Ile Pro Phe Phe His Ala Gly Asp Glu Ile Leu Arg Ser Lys Ser Leu
             355                 360                 365

Asp Arg Asp Ser Tyr Asp Ser Gly Asp Trp Phe Asn Lys Ile Asp Phe
             370                 375                 380

Thr Tyr Glu Thr Asn Asn Trp Gly Val Gly Leu Pro Pro Arg Glu Lys
385                  390                 395                 400

Asn Glu Gly Ser Trp Pro Leu Met Lys Pro Arg Leu Glu Asn Pro Ser
                 405                 410                 415

Phe Lys Pro Ala Lys His Asp Ile Ile Ala Ala Leu Asp Lys Phe Ile
             420                 425                 430

Asp Ile Leu Lys Ile Arg Tyr Ser Ser Pro Leu Phe Arg Leu Thr Thr
             435                 440                 445
```

```
Ala Ser Asp Ile Val Gln Arg Val His Phe His Asn Thr Gly Pro Ser
    450                 455                 460

Leu Val Pro Gly Val Ile Val Met Ser Ile Glu Asp Ala Arg Asn Asp
465                 470                 475                 480

Arg His Asp Met Ala Gln Ile Asp Glu Thr Phe Ser Cys Val Val Thr
                485                 490                 495

Val Phe Asn Val Cys Pro Tyr Glu Val Ser Ile Glu Ile Pro Asp Leu
                500                 505                 510

Ala Ser Leu Arg Leu Gln Leu His Pro Val Gln Val Asn Ser Ser Asp
            515                 520                 525

Ala Leu Ala Arg Gln Ser Ala Tyr Asp Thr Ala Thr Gly Arg Phe Thr
            530                 535                 540

Val Pro Lys Arg Thr Ala Ala Val Phe Val Glu Pro Arg Cys
545                 550                 555
```

(2) INFORMATION FOR SEQ ID NO: 3:

(i) SEQUENCE CHARACTERISTICS:
        (A) LENGTH: 492 base pairs
        (B) TYPE: nucleotide
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Solanum tuberosum
        (B) STRAIN: Berolina
        (F) TISSUE TYPE: tuber (ix) FEATURE:
        (A) NAME/KEY: CDS
        (B) LOCATION:1..492
        (D) OTHER INFORMATION:/product= "debranching enzyme
        (R-enzyme)"

(xi) SEQUENCE DESCRIPTION: SEQ ID NO: 3:

```
TCT GCT GAT GGC AAG TGG ACA TTA TTA GTT AAT CTT GAT TCT GAT GAT       48
Ser Ala Asp Gly Lys Trp Thr Leu Leu Val Asn Leu Asp Ser Asp Asp
560                 565                 570

GTA AAA CCT GAA GGC TGG GAT AAT CTA CAA GAC GTG AAG CCA AAT CTT       96
Val Lys Pro Glu Gly Trp Asp Asn Leu Gln Asp Val Lys Pro Asn Leu
575                 580                 585                 590

CTT TCC TTT TCT GAT GTC AGC ATC TAT GAG CTG CAT GTT AGA GAT TTC      144
Leu Ser Phe Ser Asp Val Ser Ile Tyr Glu Leu His Val Arg Asp Phe
                595                 600                 605

ACT GCC AGT GAC CCT ACT GTG TCT CAT GAA TTT CAG GCC GGT TAT CTC      192
Thr Ala Ser Asp Pro Thr Val Ser His Glu Phe Gln Ala Gly Tyr Leu
            610                 615                 620

GCC CCT TCC ACG TCG CAG GCA TCA GCT GGT GTC CAA CAT TTG AAA AGA      240
Ala Pro Ser Thr Ser Gln Ala Ser Ala Gly Val Gln His Leu Lys Arg
            625                 630                 635

TTA TCA AGT GCT GGT ATC ACT CAT GTC CAC CTG TGG CCA ACC TAT CAA      288
Leu Ser Ser Ala Gly Ile Thr His Val His Leu Trp Pro Thr Tyr Gln
            640                 645                 650

TTT GCT GGT GTC GAA GAT GAG AAA CAT AAA TGG AAG TAT ACA GAT ATC      336
Phe Ala Gly Val Glu Asp Glu Lys His Lys Trp Lys Tyr Thr Asp Ile
655                 660                 665                 670

GAG AAA CTC AAC TCT TTT CCA CCA GAT TCT GAG GAG CAG CAG GCT CTT      384
Glu Lys Leu Asn Ser Phe Pro Pro Asp Ser Glu Glu Gln Gln Ala Leu
```

```
                              675                 680                 685
ATC ACA GCC ATC CAA GAT GAA GAT GGC TAT AAT TGG GGG TAT AAT CCT             432
Ile Thr Ala Ile Gln Asp Glu Asp Gly Tyr Asn Trp Gly Tyr Asn Pro
            690                 695                 700

GTT CTC TGG GGA GTT CCA AAG GGA AGC TAT GCT GGT AAT GCA AAT GGT             480
Val Leu Trp Gly Val Pro Lys Gly Ser Tyr Ala Gly Asn Ala Asn Gly
        705                 710                 715

CCT TGT CGT ATC                                                             492
Pro Cys Arg Ile
    720

(2) INFORMATION FOR SEQ ID NO: 4:

(i) SEQUENCE CHARACTERISTICS:
        (A) LENGTH: 164 amino acids
        (B) TYPE: amino acid
        (D) TOPOLOGY: linear (ii) MOLECULE TYPE: protein (xi) SEQUENCE DESCRIPTION: SEQ ID NO: 4:

Ser Ala Asp Gly Lys Trp Thr Leu Leu Val Asn Leu Asp Ser Asp Asp
 1               5                  10                  15

Val Lys Pro Glu Gly Trp Asp Asn Leu Gln Asp Val Lys Pro Asn Leu
             20                  25                  30

Leu Ser Phe Ser Asp Val Ser Ile Tyr Glu Leu His Val Arg Asp Phe
         35                  40                  45

Thr Ala Ser Asp Pro Thr Val Ser His Glu Phe Gln Ala Gly Tyr Leu
     50                  55                  60

Ala Pro Ser Thr Ser Gln Ala Ser Ala Gly Val Gln His Leu Lys Arg
65                  70                  75                  80

Leu Ser Ser Ala Gly Ile Thr His Val His Leu Trp Pro Thr Tyr Gln
             85                  90                  95

Phe Ala Gly Val Glu Asp Glu Lys His Lys Trp Lys Tyr Thr Asp Ile
            100                 105                 110

Glu Lys Leu Asn Ser Phe Pro Pro Asp Ser Glu Glu Gln Gln Ala Leu
        115                 120                 125

Ile Thr Ala Ile Gln Asp Glu Asp Gly Tyr Asn Trp Gly Tyr Asn Pro
    130                 135                 140

Val Leu Trp Gly Val Pro Lys Gly Ser Tyr Ala Gly Asn Ala Asn Gly
145                 150                 155                 160

Pro Cys Arg Ile
```